US006242570B1

(12) United States Patent
Sytkowski (10) Patent No.: US 6,242,570 B1
(45) Date of Patent: Jun. 5, 2001

(54) PRODUCTION AND USE OF RECOMBINANT PROTEIN MULTIMERS WITH INCREASED BIOLOGICAL ACTIVITY

(75) Inventor: Arthur J. Sytkowski, Arlington, MA (US)

(73) Assignee: Beth Israel Deaconess Medical Center, Boston, MA (US)

(*) Notice: Subject to any disclaimer, the term of this patent is extended or adjusted under 35 U.S.C. 154(b) by 0 days.

(21) Appl. No.: 08/890,929

(22) Filed: Jul. 10, 1997

(51) Int. Cl.[7] .......................... A61K 38/18; C12N 15/00; C07K 14/505

(52) U.S. Cl. .............................. 530/350; 514/2; 514/12; 514/18; 514/19; 435/69.1; 435/69.6; 435/69.7; 435/320.1; 530/350; 530/402

(58) Field of Search .................... 514/2, 12, 18, 514/19; 435/69.1, 69.5, 59.6, 59.7, 320.1; 530/351, 402

(56) References Cited

U.S. PATENT DOCUMENTS

| | | | |
|---|---|---|---|
| 4,816,567 | 3/1989 | Cabilly et al. | 530/387 |
| 4,874,813 | 10/1989 | O'Shannessy | 525/54.1 |
| 5,073,627 | 12/1991 | Curtis et al. | 530/351 |
| 5,091,513 | 2/1992 | Huston et al. | 530/387 |
| 5,114,711 | 5/1992 | Bell et al. | 424/85.1 |
| 5,116,964 | 5/1992 | Capon et al. | 536/27 |
| 5,225,538 | 7/1993 | Capon et al. | 530/387.3 |
| 5,349,053 | 9/1994 | Landolfi | 530/351 |
| 5,428,130 | 6/1995 | Capon et al. | 530/350 |
| 5,547,852 | 8/1996 | Seiler et al. | 435/29 |
| 5,580,853 | 12/1996 | Sytkowski | 514/8 |
| 5,614,184 | 3/1997 | Sytkowski et al. | 424/85.1 |
| 5,684,136 | 11/1997 | Godowski | 530/399 |
| 5,747,446 | * 5/1998 | Sytkowski | 514/8 |
| 5,883,230 | 3/1999 | Schendel | 530/351 |

FOREIGN PATENT DOCUMENTS

| | | |
|---|---|---|
| 79357 | 1/1992 | (AU) . |
| 0 283 244 B1 | 3/1988 | (EP) . |
| 0 464 533 A1 | 6/1991 | (EP) . |
| 0 464 533 B1 | 6/1991 | (EP) . |
| 0 622 459 A1 | 4/1994 | (EP) . |
| 0618227A1 | 5/1994 | (EP) . |
| 0 816 510 | 12/1996 | (EP) . |
| WO 91/19739 | 12/1991 | (WO) . |
| WO 92/04455 | * 3/1992 | (WO) . |
| 92/06117 | 4/1992 | (WO) . |
| WO 92/03116 | 4/1992 | (WO) . |
| WO 94/02611 | 2/1994 | (WO) . |
| 94/09817 | 5/1994 | (WO) . |
| 94/13806 | 6/1994 | (WO) . |
| WO 95/33057 | * 12/1995 | (WO) . |
| WO 96/19573 | 6/1996 | (WO) . |
| 97/00319 | 1/1997 | (WO) . |
| WO 97/12985 | 4/1997 | (WO) . |

OTHER PUBLICATIONS

Yamaguchi, K., et al., "Effects of Site–directed Removal of N–Glycosylation Sites in Human Erythropoietin on Its Production and Biological Properties," *J. Biol. Chem.*, 266(30):20434–20439, (Oct. 25, 1991).

Curtis, B., et al., "Enhanced hematopoietic activity of a human granulocyte/macrophage colony–stimulating factor–interleukin 3 fusion protein," *Proc. Natl. Acad. Sci. USA*, 88:5809–5813, (Jul., 1991).

Boissel, J.P., et al., "Erythropoietin Structure–Function Relationships," In *The Biology of Hematopoiesis*, (Wiley–Liss, Inc.), pp. 227–232 (1990).

Dubé, S., et al., "Glycosylation at Specific Sites of Erythropoietin Is Essential for Biosynthesis, Secretion, and Biological Function," *J. Biol. Chem.*, 263(33):17516–17521 (Nov. 25, 1988).

Wen, D., et al., "Erythropoietin Structure–Function Relationships: High Degree of Sequence Homology Among Mammals," *Blood*, 82(5): 1507–1516, (Sep. 1, 1993).

Wen, D., et al., "Erythropoietin Structure–Function Relationships: Identification of Functionally Important Domains," *J. Biol. Chem.*, 269(36): 22839–22846, (Sep. 9, 1994).

Boissel, J.P., et al., "Erythropoietin Structure–Function Relationships: Mutant Proteins That Test A Model of Tertiary Structure," *J. Biol. Chem.*, 268(21): 15983–15993, (Jul. 25, 1993).

Chern, Y., et al., "Potentiation of the Erythropoietin Response by Dimethyl Sulfoxide Priming of Erythroleukemia Cells: Evidence for Interaction of Two Signaling Pathways," *Blood*, 76(11):2204–2209, (Dec. 1, 1990).

Sytkowski, A., et al., "Immunochemical Studies of Human Erythropoietin Using Site–Specific Anti–peptide Antibodies: Identification of a Functional Domain," *J. Biol. Chem.*, 262(3): 1161–1165, (Jan. 25, 1987).

Sytkowski, A., et al., "Isolation and Characterization of an Anti–peptide Monoclonal Antibody to Human Erythropoietin," *J. Biol. Chem.*, 260(27): 14727–14731, (Nov. 25, 1985).

Feldman, L., et al., "Four Unique Monoclonal Antibodies to the Putative Receptor Binding Domain of Erythropoietin Inhibit the Biological Function of the Hormone," *Exp. Hematol.*, 20:64–68, (1992).

(List continued on next page.)

*Primary Examiner*—Anthony Caputa
*Assistant Examiner*—Karen A. Canella
(74) *Attorney, Agent, or Firm*—Hamilton, Brook, Smith & Reynolds, P.C.

(57) ABSTRACT

The invention relates to novel recombinant fusion proteins comprising two or more erythropoietin molecules. The fusion proteins can be linked by a peptide linker. The fusion proteins can be used, for example, to treat or prevent anemia in a mammal. Also disclosed are nucleotide sequences encoding the fusion proteins vectors comprising the nucleic acid sequences of the fusion proteins and host cells transfected with the vectors.

13 Claims, 6 Drawing Sheets

OTHER PUBLICATIONS

Fibi, M.R., et al., "N–and O–Glycosylation Muteins of Recombinant Human Erythropoietin Secreted from BHK–21 Cells," *Blood*, 85(5): 1229–1236, (Mar. 1, 1995).

Takeuchi, M., et al., "Role of Sugar Chains in the in Vitro Biological Activity of Human Erythropoietin Produced in Recombinant Chinese Hamster Ovary Cells," *J. Biol. Chem.*, 265(21): 12127–12130, (Jul. 25, 1990).

Yonekura, S., et al., "Erythropoietin receptors induced by dimethyl sulfoxide exhibit positive cooperativity associated with an amplified biologic response," *Proc. Natl. Acad. Sci. USA*, 88:2535–2539, (Mar. 1991).

Grodberg, J., et al., "Functional and Structural Role of Arginine 103 in Human Erythropoietin," *Arch. Bioch. Bioph.*, 333(2): 427–431, (Sep. 15, 1996).

Chern, Y., et al., "Structural Role of amino acids 99–110 in recombinant human erythropoietin," *Eur. J. Biochem.*, 202: 225–229, (1991).

Grodberg, J., et al., "Alanine scanning mutagenesis of human erythropoietin identifies four amino acids which are critical for biological activity," *Eur. J. Biochem.*, 218: 597–601, (1993).

Jacobs, K., et al., "Isolation and characterization of genomic and cDNA clones of human erythropoietin," *Nature*, 313:806–810, (Feb. 28, 1985).

Hollenbaugh, D., et al., "Cleavable CD40Ig fusion proteins and the binding to sgp39," *J. Immuno. Meth.*, 188: 1–7 (1995).

Sandlie, I., et al., "Engineering the Hinge Region to Optimize Complement–induced Cytolysis," In *Antibody Engineering*, C.A.K. Borrebaeck, eds. (NY: W.H. Freeman and Company) pp. 69–88 (1992).

Hamers–Castermann, C., et al., "Naturally occurring antibodies devoid of light chains," *Nature*, 363: 446–448, (Jun. 2, 1993).

Terskjkh, A.V., et al., "Peptabody: A new type of high avidity binding protein," *Proc. Natl. Acad. Sci. USA*, 94:1663–1668, (Mar. 1997).

McMahon, F.G., et al., "Pharmacokinetics and Effects of Recombinant Human Erythropoietin After Intravenous and Subcutaneous Injections in Healthy Volunteers," *Blood*, 76(9): 1718–1722, (Nov. 1, 1990).

Spivak, J.L., et al., "The In Vivo Metabolism of Recombinant Human Erythropoietin in the Rat," *Blood*, 73(1): 90–99, (Jan. 1989).

Knusli, C., et al., "Polyethylene glycol (PEG) modification of granulocyte–macrophage colony stimulating factor (GM–CSF) enhances neutrophil priming activity but not colony stimulating activity," *British Journal Haematology*, 82: 654–663, (1992).

Satake, R., et al., "Chemical modification of erythropoietin: an increase in in vitro activity by guanidination," *Biochimica et Biophysica Acta*, 1038: 125–129, (1990).

Sytkowski, A.J., et al., "An Epo—Epo Fusion Protein with Enhanced Potency and Efficacy in vivo," Thirty–Ninth Annual Meeting of the American Society of Hematology, San Diego, California, USA, Dec. 5–9, 1997. *Blood 90 (10 Suppl. 1 Part 1)*. 1997. 57A. (Abstract 244).

Lunn, E.D., et al., "Erythropoietin Dimers with Enhanced in vivo Activity in Mice," Thirty–Eighth Annual Meeting of the American Society of Hematology, Orlando, Florida, USA, Dec. 6–10, 1996. *Blood* 88 (10 Suppl. 1 Part 1–2). 1996. 543A. (Abstract 2161).

McGary, E.C., et al., "Post–transcriptional Regulation of Erythropoietin mRNA Stability by Erythropoietin mRNA–binding Protein," *The Journal of Biological Chemistry*, 272:8628–8634 (1997).

Batra, J.K., et al., "Insertion of Constant Region Domains of Human $IgG_1$ Into CD4–PE40 Increases its Plasma Half–Life," *Molecular Immunology*, 30:379–386 (1993).

Jelkmann, W., "Biology of Erythropoietin," *Clin Investig*, 72:S3–S10 (1994).

Modi, N.B., "Pharmacokinetics and pharmacodynamics of recombinant proteins and peptides", *Journal of Controlled Release*, 29:269–281 (1994).

Stykowski, A.J., et al., "Human erythropoiein dimers with markedly enhanced in vivo activity", *Proc. Natl. Acad. Sci. USA* 95:1184–1188.*

* cited by examiner

FIG. 6  BgII restriction digests: ① EpoA^IV Forward Direction ⊕
2396bp, 1461bp, 305bp ② EpoA^IV Reverse Direction ⊖
2051bp, 1806bp, 305bp FIG. 7  BgII restriction digests: ① EpoB^I Forward Direction ⊕
2356bp, 1381bp, 305bp ② EpoB^I Reverse Direction ⊖
1971bp, 1766bp, 305bp FIG. 8 ScaI and XhoI restriction digests: 3485bp, 6776bp FIG. 9 BamHI and ScaI restriction digests: 3485bp, 5576bp FIG. 10 XhoI and BamHI restriction digest: 5376bp, 56bp

FIG. 11

NgoMI restriction digest of pcDNA3-1-Epo-Epo: 3931bp, 1342bp, 1054bp, 2836bp

SEQUENCE LISTING

```
<160> NUMBER OF SEQ ID NOS: 9

<210> SEQ ID NO: 1
<211> LENGTH: 17
<212> TYPE: PRT
<213> ORGANISM: Unknown
<220> FEATURE:
<223> OTHER INFORMATION: Synthetic

<400> SEQUENCE: 1

Ala Gly Gly Gly Gly Ser Gly Gly Gly Ser Gly Gly Gly Gly Ser
 1               5                  10                  15

Thr

<210> SEQ ID NO: 2
<211> LENGTH: 20
<212> TYPE: DNA
<213> ORGANISM: Synthetic

<400> SEQUENCE: 2
gccggcggtg gtggatctgg                                           20

<210> SEQ ID NO: 3
<211> LENGTH: 22
<212> TYPE: DNA
<213> ORGANISM: Synthetic

<400> SEQUENCE: 3
aggcgcggag atgggggtgc ac                                        22

<210> SEQ ID NO: 4
<211> LENGTH: 40
<212> TYPE: DNA
<213> ORGANISM: Synthetic

<400> SEQUENCE: 4
ccagatccac caccgccggc tctgtcccct gtcctgcagg                     40
```

```
<210> SEQ ID NO: 5
<211> LENGTH: 40
<212> TYPE: DNA
<213> ORGANISM: Synthetic

<400> SEQUENCE: 5
cgccaccgga tccaccgcca ccagatccac caccgccggc                              40

<210> SEQ ID NO: 6
<211> LENGTH: 39
<212> TYPE: DNA
<213> ORGANISM: Synthetic

<400> SEQUENCE: 6
tggtggggca gtactgccgc cgccaccgga tccaccgcc                               39

<210> SEQ ID NO: 7
<211> LENGTH: 38
<212> TYPE: DNA
<213> ORGANISM: Synthetic

<400> SEQUENCE: 7
gcggcagtac tgccccacca cgcctcatct gtgacagc                                38

<210> SEQ ID NO: 8
<211> LENGTH: 22
<212> TYPE: DNA
<213> ORGANISM: Synthetic

<400> SEQUENCE: 8
caggtggaca cacctggtca tc                                                 22

<210> SEQ ID NO: 9
<211> LENGTH: 15
<212> TYPE: PRT
<213> ORGANISM: Unknown
<220> FEATURE:
<223> OTHER INFORMATION: Synthetic

<400> SEQUENCE: 9

Gly Gly Gly Gly Ser Gly Gly Gly Gly Ser Gly Gly Gly Gly Ser
 1               5                  10                  15
```

PRODUCTION AND USE OF RECOMBINANT PROTEIN MULTIMERS WITH INCREASED BIOLOGICAL ACTIVITY

GOVERNMENT FUNDING

This invention was made, in whole or in part, with Government support under Contract No. N000014-93-1-0776 awarded by the Department of the Navy and National Institutes of Health Grant No. R01 DK38841. The Government has certain rights in the invention.

BACKGROUND OF THE INVENTION

A problem encountered in the practice of medicine when using proteins as injectable pharmaceuticals is the frequency at which those injections must be made in order to maintain a therapeutic level of the protein in the circulation. For example, erythropoietin has a relatively short plasma half-life (Spivak, J. L., and Hogans, B. B., *Blood*, 73:90 (1989); McMahon, F. G., et al., *Blood*, 76:1718(1990)). Therefore, therapeutic plasma levels are rapidly decreased, and repeated intravenous administrations must be made. An alternative route of administration is subcutaneous injection. This route offers slower absorption from the site of administration, thus causing a sustained release effect. However, significantly lower plasma levels are achieved and, thus, a similar frequency of injection, as is required with intravenous administration, must be used to produce a comparable therapeutic effect.

Modification of naturally occurring proteins which have therapeutic value is often attempted in an effort to increase the protein's biological activity. Several methods have been employed to increase the biological activity of therapeutic proteins. These methods often focus on increasing the size of the therapeutic agents. For example, the size of a protein can be increased through chemical conjugation with a reagent such as polyethylene glycol (PEG) (Knusli, C. et al., *Brit. J. Haematol*, 82:654–663 (1992)). This procedure, also known as "PEGylation", has been reported with several protein agents, first as a means to reduce antigenicity, but also as a way to increase biological activity.

Another method of increasing a protein's size is through chemical cross-linking with another protein. For example, to increase the antigenicity of a protein, chemical cross-linking agents are used to conjugate the immunogenic protein to a carrier molecule such as immunoglobulin or serum albumin.

However, the conjugation of chemical compounds or inert molecules to a protein often results in a significant decrease of the overall biological activity, and of selected biological activity of the protein. (Knusli, C., et al., *Brit. J. Haematol.*, 82:654–663 (1992)). These conjugations must be designed such that the resulting modified protein remains therapeutically efficacious and retains the desired biological properties of the unmodified, wild type (i.e., naturally-occurring) protein (Satake, R., et al., *Biochem. Biophys. Acta.* 1038:125–129 (1990)). Thus, it would be advantageous to be able to modify therapeutically active proteins to increase their biological activity which would result in less frequent injections or smaller doses of protein.

SUMMARY OF THE INVENTION

The present invention relates to modified proteins or polypeptides with increased biological activity, and methods of producing and using these modified proteins and polypeptides.

Increased biological activity results from the production of fusion proteins that result in protein multimers, e.g, dimers and trimers. Protein multimers are produced by expressing tandemly linked nucleic acids encoding the proteins of the present invention, or biologically active fragments, analogs, variants, mutants or derivatives of the proteins. The nucleic acids that encode the proteins are fused, as described herein. The proteins of the present invention can be fused directly to another protein, or can be fused via a linker, e.g., a peptide linker. The tandemly fused nucleic acid sequence is then inserted into an expression vector and introduced into a competent cell, either prokaryotic or eukaryotic, resulting in the production of a fusion protein multimer with increased biological activity.

Increased biological activity is defined herein as a prolonged plasma half-life (that is, a longer circulating half-life relative to the naturally occurring protein), and/or higher potency (i.e., requiring a smaller quantity relative to the naturally occurring protein to achieve a specified level of biological activity). Increased biological activity can also encompass a combination of the above-described activities, for example, a modified protein with higher potency that also exhibits a prolonged circulating half-life. Because the proteins of the present invention have increased biological activity, the frequency with which they must be administered is reduced, or the amount administered to achieve an effective dose is reduced. Additional advantages can also result from the modifications described herein. For example, new unpredictable activities can result, such as increased affinity for receptors or binding ligands, which can result in increased stimulation of signal generated by such binding. A reduced quantity of modified protein would then be necessary over the course of treatment as compared to the quantity necessary if unmodified protein were used.

Proteins encompassed by the present invention include any protein with therapeutic activity. Specifically encompassed by the present invention are cytokines, growth factors, and hormones which include, for example, the following: Interferon-$\alpha$, Interferon-$\beta$, Interferon-$\gamma$, Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin-12, Interleukin-13, Interleukin-14, Interleukin-15, Interleukin-16, Erythropoietin, Colony-Stimulating Factor-1, Granulocyte Colony-stimulating Factor, Granulocyte-Macrophage Colony-Stimulating Factor, Leukemia Inhibitory Factor, Tumor Necrosis Factor, Lymphotoxin, Platelet-Derived Growth Factor, Fibroblast Growth Factors, Vascular Endothelial Cell Growth Factor, Epidermal Growth Factor, Transforming Growth Factor-$\beta$, Transforming Growth Factor-$\alpha$, Thrombopoietin, Stem Cell Factor, Oncostatin M, Amphiregulin, Mullerian-Inhibiting Substance, B-Cell Growth Factor, Macrophage Migration Inhibiting Factor, Endostatin, and Angiostatin. Descriptions of these proteins can be found in Human Cytokines: Handbook for Basic and Clinical Research, Aggarwal, B. B. and Gutterman, J. U. Eds., Blackwell Scientific Publications, Boston, Mass., (1992), which is herein incorporated by reference in its entirety.

More specifically, the present invention relates to modified erythropoietin with increased biological activity, as defined herein. The modified erythropoietin with increased biological activity of the present invention is a fusion protein comprising two or more erythropoietin molecules covalently fused, resulting in an erythropoietin multimer.

Also encompassed by the present invention are methods of making and using the fusion protein multimers described herein and methods of using them.

DETAILED DESCRIPTION OF THE INVENTION

As used herein, the term "fusion protein" refers to a C-terminal to N-terminal fusion of one protein molecule to another protein molecule. The fusion proteins of the present invention typically include constructs in which a linker peptide sequence is utilized. The fusion proteins of the present invention have a formula of $R_1$–$R_2$ or $R_1$—L—$R_2$, where $R_1$ and $R_2$ are substantially similar or identical protein molecules and L is a linker, typically a peptide. In another embodiment of the present invention, $R_1$ and $R_2$ can be different proteins. The protein molecules are fused to one another in such a manner as to produce a single fusion protein comprised of two or more protein molecules.

The fusion protein produced has increased biological activity. In one embodiment of the present invention the protein molecules are EPO.

Fusion protein constructs are named by listing the respective molecules. For example, EPO-L-EPO refers to a fusion protein comprised of two EPO molecules joined by a peptide linker, and EPO-L-EPO-L-EPO refers to a fusion protein comprised of three EPO molecules joined by two peptide linkers.

The term "recombinant," as used herein, means that a protein is derived from recombinant (e.g., microbial or mammalian) expression systems. "Microbial" refers to recombinant proteins made in bacterial, fungal, e.g. yeast, or insect expression systems. Proteins expressed in most bacterial cultures will be free of glycan. Protein expressed in yeast may have a glycosylation pattern different from protein expressed in mammalian cells.

As used herein, the term "nucleotide sequence" or "nucleic acid sequence" refers to a heteropolymer of deoxyribonucleotides (DNA) or ribonucleotides (RNA). Nucleic acid sequences encoding the proteins provided in this invention can be assembled from DNA, either cDNA or genomic DNA, or RNA, and short oligonucleotide linkers to provide a synthetic nucleic acid sequence which is capable of being expressed in a recombinant transcriptional unit.

The term "recombinant expression vector," as used herein, refers to a replicable DNA construct used either to amplify or to express DNA which encodes the fusion proteins of the present invention. The recombinant expression vector includes a transcriptional unit comprising an assembly of (1) a genetic element or elements having a regulatory role in gene expression, for example, promoters or enhancers; (2) a structural or coding sequence which is transcribed into mRNA and translated into protein; and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader sequence or transport sequence, it may include an N-terminal methionine residue. This residue may optionally be subsequently cleaved from the expressed recombinant protein to provide a final product.

A DNA sequence encoding a fusion protein is constructed using recombinant DNA techniques to assemble separate DNA fragments encoding proteins into an appropriate expression vector. For example, the 3' end of a DNA molecule encoding a protein is ligated to the 5' end of a second DNA molecule encoding the same or a substantially similar protein, with the reading frames of the sequences in phase to permit mRNA translation of the sequences into a single biologically active fusion protein. The DNA molecules are joined in tandem, meaning that the DNA molecules are joined in succession, one after the other. The regulatory elements responsible for transcription of DNA into mRNA are retained on the first of the two DNA sequences while binding signals or stop codons, which would prevent read-through to the second DNA sequence, are eliminated. Conversely, regulatory elements are removed from the second DNA sequence while stop codons required to end translation are retained.

As described herein, means are provided for linking protein molecules, preferably via a linker sequence(s). The linker sequence(s) separates the protein molecules by a distance sufficient to ensure that each protein molecule properly folds into its secondary and tertiary structures. Suitable linker sequences (1) adopt a conformation suitable to result in a fusion protein with increased biological activity, (2) do not exhibit a propensity for developing an ordered secondary structure which could impair the biological functions of the protein molecules, and (3) have minimal hydrophobic or charged character which could impair the biological functions of the EPO molecules. For example, a suitable linker will produce a fusion protein where interaction of the protein components results in increased biological activity. The linker conformation can be flexible or rigid, depending on the final conformation of the fusion required to result in increased biological activity. An example of a more rigid linker would be a linker with an α-helix that would not allow free rotation of the linked protein components. Typical surface amino acids in flexible protein regions include Glycine (Gly), Asparagine (Asn) and Serine (Ser). Virtually any permutation of amino acid sequences containing Glycine (Gly), Asparagine (Asn) and Serine (Ser) would be expected to satisfy the above criteria for linker sequence. Other near neutral amino acids, such as Threonine (Thr) and Alanine (Ala), may also be used in the linker sequence.

The length of the linker sequence may vary without significantly affecting the biological activity of the fusion protein. Generally, the protein, e.g., EPO, molecules will be separated by a linker sequence having a length of about 10 amino acids to about 20 amino acids, although longer linker sequences may be used, for example, a full-length polypeptide can comprise the linker. In the most preferred aspects of the present invention, the linker sequence is about 15 amino acids in length. The linker sequence is incorporated into the fusion protein by well-known methods and as described in the "materials and methods" section below.

In one embodiment, the fusion proteins described herein comprise wild type (e.g., naturally-occurring) proteins with therapeutic activity. As defined herein, therapeutic activity means the ability of a fusion protein, upon administration to a mammal, to alleviate, to any degree, or eliminate the deficiency or condition for which the mammal is being treated. Specifically encompassed by the present invention are cytokines, growth factors, and hormones which include, for example, the particular proteins listed in the following paragraphs followed by the appropriate reference(s). Each of the references in the following paragraphs is incorporated by reference in its entirety.

INTERFERON-α: Henco, K., et al., J. Mol. Biol., 185: 227–260 (1985). Pestka, S., et al., Ann. Rev. Biochem., 56: 727–777 (1987). Methods in Enzymology, Pestka, S. (Ed.), Academic Press, New York, N.Y., vol. 119, pp. 3–14 (1986).

INTERFERON-β: Human Cytokines: Handbook for Basic and Clinical Research, Aggarwal, B. B. and Gutterman, J. U. (Eds.), Blackwell Scientific Publications, Boston, Mass. (1992).

INTERFERON-γ: Gray, P. W., et al., Nature, 298:859–863 (1982). Rinderknecht, E. et al., J. Biol. Chem., 259:6790–6797 (1984).

INTERLEUKIN-1: IL-1α: Furutani, Y., et al., Nucleic Acids Res., 143:167–3179 (1986). IL-1β: Clark, B. D., et al., Nucleic Acids Res. 14:7897–7914 (1986).

INTERLEUKIN-2: Fujita et al., 1983. Durand, D. B., et al., Mol. Cell Biol., 8:1715–1724 (1988).

INTERLEUKIN-3: Yang, Y. C., et al., Cell, 47:3–10 (1986).

INTERLEUKIN-4: Arai, N., et al., J. Immunol., 142:274–282 (1989).

INTERLEUKIN-5: Azuma, C., et al., Nucleic Acids Res., 14:9149–9158 (1986). Yokota, T., et al., Proc. Natl. Acad. Sci. USA, 84:7388–7392 (1987).

INTERLEUKIN-6: Hirano, T., et al., Nature, 324:73–76 (1986). Van Snick, J., et al., Eur. J. Immunol., 18:193–197 (1988).

INTERLEUKIN-7: Goodwin, R. G., et al., Proc. Natl. Acad. Sci. USA, 86(l):302–306 (1989).

INTERLEUKIN-8: King, C. H., et al., UNPUBLISHED.

INTERLEUKIN-9: Renauld, J- C., et al., J. Immunol., 144:4235–4241 (1990). Moeller, J., et al., J. Immunol. 144:4231–4234 (1990). Yang, Y. C., et al., Blood, 74:1880–1884 (1989).

INTERLEUKIN-10: Moore, K. W., et al., Science, 248:1230–1234 (1990). Fiorentino, D. F., et al., J. Exp. Med., 170:2081–2095 (1989).

INTERLEUKIN-11: Paul, S. R., et al., Proc. Natl. Acad. Sci. USA, 87(19):7512–7516 (1990).

INTERLEUKIN-12: Wolf, S. F., et al., J. Immunol., 146(9):3074–3081 (1991); BLAST Database (www.ncib.nlm.nih.gov), accession number M65290.

INTERLEUKIN-13: Dolganov, G., Blood, 87(8):3316–3326 (1996).

INTERLEUKIN-14: Ambrus, J. L., et al., Proc. Natl. Acad. Sci. USA, 90(13):6330–4 (1993).

INTERLEUKIN-15: Meazza, R., et al., Oncogene, 12(10):2187–2192 (1996).

INTERLEUKIN-16: Cruikshank, W. W., et al., Proc. Natl. Acad. Sci. USA, 91(11):5109–5113 (1994).

ERYTHROPOIETIN: Jacobs, K., et al., Nature, 313:806–810 (1985).

COLONY-STIMULATING FACTOR-1: Kawasaki, E. S., et al., Science, 230:291–296 (1985). Wong, G. G., et al., Science, 235:1504–1508 (1987). Ladner, M. B., et al., EMBO. J., 6:2693–2698 (1987). Cerretti, D. P., et al., Mol. Immunol., 25:761–770 (1988). Colony Stimulating Factors, Dexter, T. M., et al. (Eds.), Marcel Dekker Publishers, New York, N.Y. pp. 155–176 (1990).

GRANULOCYTE-COLONY-STIMULATING FACTOR: Nagata, S., et al., Nature, 319:415–418 (1986). Souza, L. M., et al., Science, 232:61–65 (1986).

GRANULOCYTE-MACROPHAGE COLONY-STIMULATING FACTOR: Miyataka, S., et al., EMBO J., 4:2561–2568 (1985).

LEUKEMIA INHIBITORY FACTOR: Moureau, J- F., et al., Nature, 336:690–692 (1988).

TUMOR NECROSIS FACTOR: Nedwin, G. E., et al., Nucl. Acids Res., 13:6361–6373 (1985).

LYMPHOTOXIN: Nedwin, G. E., et al., J. Cell Biochem., 29:171–182 (1985).

PLATELET-DERIVED GROWTH FACTOR: Deuel, T. F., et al., J. Biol. Chem., 256:8896–8899 (1981). Human Cytokines: Handbook for Basic and Clinical Research, Aggarwal, B. B. and Gutterman, J. U. (Eds.), Blackwell Scientific Publications, Boston, Mass. (1992).

FIBROBLAST GROWTH FACTORS: Abraham, J. A. , et al., Science, 233:545–547 (1986a).

VASCULAR ENDOTHELIAL CELL GROWTH FACTOR: Keck, P. J., et al., Science, 246:1309–1312 (1989).

EPIDERMAL GROWTH FACTOR: Scott, J., et al., Science, 221:236–240 (1983). Gray, A., et al., Nature, 303:722–725 (1983).

TRANSFORMING GROWTH FACTOR-β: Derynck, R., et al., Nature, 316:701–705 (1985). Scotto, L., et al., J. Biol. Chem., 265:2203–2208 (1990).

TRANSFORMING GROWTH FACTOR-α: Derynck, R., Cell, 54:593–595 (1988).

THROMBOPOIETIN: Sohma, Y., et al., FEBS Lett., 353(1): 57–61 (1994); BLAST Database (www.ncib.nlm.nih.gov), accession number D32046.

STEM CELL FACTOR: Williams, D. E., et al., Cell, 63:167–174 (1990). Copeland, N. G., et al., Cell, 63:174–183 (1990). Flanagan, J. G., et al., Cell, 63:185–194 (1990). Zsebo, K. M., et al., Cell, 63:213–224 (1990). Martin, F. H., et al., Cell, 63:203–211 (1990). Zsebo, K. M., et al., Cell, 63:195–201 (1990). Huang, E., et. al., Cell, 63:225–233 (1990). Anderson, D. M., et al., Cell, 63:235–243 (1990).

ONCOSTATIN M: Linsley, P. S., et al., Mol. Cell. Biol., 10:1882–1890 (1990). Zarling, J. M., et al., Proc. Natl. Acad. Sci. USA, 83:9739–9743 (1986). Malik, N., et al., Mol. Cell. Biol., 9:2847–2853 (1989).

AMPHIREGULIN: Plowman, G. D., et al., Mol. Cell. Biol., 10:1969–1981 (1990). Shoyab, M., et al., Proc. Natl. Acad. Sci. USA, 85:6528–6532 (1988).

MULLERIAN-INHIBITING SUBSTANCE: Cate, R. L., et al., Cell, 45:685–698 (1986). Wallen, J. W., et al., Cancer Res., 49:2005–2011 (1989). Picard, J- Y., et al., Proc. Natl. Acad. Sci. USA, 83:5464–5468 (1986). Coughlin, J. P., et al., Mol. Cell. Endocrinol., 49:75–86 (1987).

B-CELL GROWTH FACTOR: Sharma, S., et al., Molecular cloning and expression of a human B-cell growth factor gene in *Escherichia coli,* 235:1489–1492 (1987).

MACROPHAGE MIGRATION INHIBITORY FACTOR: Weiser, W. Y., et al., Proc. Natl. Acad. Sci. USA, 86:7522–7526 (1989).

ENDOSTATIN: O'Reilly, M. S., et al., Cell, 88(2):277–285 (1997).

ANGIOSTATIN: O'Reilly, M. S., et al., Cell, 79(2):315–328 (1994).

Also encompassed by the present invention are fusion proteins comprising biologically active fragments, analogs, mutants, variants or derivatives of the naturally-occurring proteins described herein. Biologically active fragments, derivatives, analogs, variants and mutants of the naturally-occurring proteins are also referred to herein as substantially similar proteins of the naturally-occurring protein. However, the level of biological activity of fragments, analogs, mutants, variants or derivatives of the naturally-occurring protein need not be identical to the activity of the naturally-occurring protein (also referred to herein as the parent protein). For example, a fragment of a cytokine protein may exhibit only 50–80% of the activity of the naturally-occurring cytokine, yet because two or more cytokines, either the same or different, are linked to form a fusion protein, the fusion protein exhibits increased biological activity as compared to a monomer of the naturally-occurring cytokine. Tests to determine biological activity are well-known to those of skill in the art and can include, for example, measuring the extent of hematopoiesis, platelet production or receptor binding. For example, the biological activity of a mutant of erythropoietin can be measured as described in U.S. Pat. Nos. 5,614,184 and 5,580,853, the teachings of which are herein incorporated by reference in their entirety.

The present invention also provides proteins with or without associated native-protein glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced carbohydrate form in good yield using yeast expression systems. N-glycosylation sites in eukaryotic proteins are characterized by the amino acid triplet Asn-$A_1$-Z, where $A_1$ is any amino acid except Proline (Pro), and Z is Serine (Ser) or Threonine (Thr). In this sequence, asparagine provides a side chain amino group for covalent attachment of carbohydrate. Such a site can be eliminated by substituting another amino acid for Asparagine (Asn) or for residue Z, deleting Asparagine (Asn) or Z, or inserting a non-Z amino acid between $A_1$ and Z, or an amino acid other than Asparagine (Asn) between Asparagine (Asn) and $A_1$.

Derivatives and analogs can be obtained by mutations of the fusion protein. A derivative or analog, as referred to herein, is a polypeptide comprising an amino acid sequence that shares sequence identity, or similarity, with the full-length sequence of the wild type (or naturally occurring protein), except that the derivative or analog has one or more amino acid sequence differences attributable to a deletion, insertion and/or substitution.

Bioequivalent analogs of proteins can be constructed by, for example, making various substitutions of residues or sequences. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered. Due to degeneracy of the genetic code, there can be considerable variation in nucleotide sequences encoding the same amino acid sequence.

Mutations in nucleotide sequences constructed for expression of analogs must, of course, preserve the reading frame phase of the coding sequences and preferably will not create complementary regions that could hybridize to produce secondary mRNA structures such as loops or hairpins which would adversely affect translation of the mRNA. Alternatively, mutations could introduce secondary structure which would result in higher translational efficiency. Although a mutation site may be predetermined, it is not necessary that the nature of the mutation per se be predetermined. For example, in order to select for optimum characteristics of mutants at a given site, random mutagenesis may be conducted at the target codon and the iexpressed mutants screened for the desired activity.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 12–19, 1985); Smith et al. (*Genetic Engineering: Principles and Methods*, Plenum Press, 1981); and U.S. Pat. Nos. 4,518,584 and 4,737,462 and are incorporated by reference herein.

The present invention also provides recombinant expression vectors which include synthetic or cDNA-derived DNA fragments encoding fusion proteins comprising DNA encoding two or more linked proteins operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated. Operably linked indicates that components are linked in such a manner that expression of the DNA encoding a fusion protein is controlled by the regulatory elements. Generally, operably linked means contiguous.

Transformed host cells are cells into which fusion protein vectors have been introduced by infectious or non-infectious methods. Transformed host cells ordinarily express the desired fusion protein, but host cells transformed for purposes of cloning or amplifying DNA do not need to express the protein. In eukaryotic cells, expressed fusion protein will generally be secreted into the culture supernatant. In prokaryotic cells, the fusion proteins may be expressed within the periplasmic space or as insoluble inclusion bodies. Suitable host cells for expression of fusion protein include prokaryotes, yeast or higher eukaryotic cells under the control of appropriate promoters. Prokaryotes include gram negative or gram positive organisms, for example *E. coli*. Higher eukaryotic cells include established cell lines of mammalian origin as described below. Cell-free translation systems could also be employed to produce fusion protein using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), which is incorporated herein by reference.

Prokaryotic expression vectors generally comprise one or more phenotypic selection markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223–3 (Pharmacia Fine Chemicals, Uppsala, Sweden) and pGEM1 (Promega Biotech, Madison, Wis.). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the blactamase (penicillinase)and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980) and tac promoter (Maniatis, *Molecular Cloning: A Laboratory Manual*, Cold Spring Harbor Laboratory, 1982).

Recombinant fusion proteins may also be expressed in yeast hosts, preferably from the Saccharomyces species, such as *S. cerevisiae*. Yeast of other genera such as Pichia or Kluyveromyces may also be employed. Yeast vectors will generally contain an origin of replication from a yeast plasmid or an autonomously replicating sequence (ARS), promoter, DNA encoding the fusion protein, sequences for polyadenylation and transcription termination and a selection gene. Preferably, yeast vectors will include an origin of replication and selectable marker permitting transformation of both yeast and *E. coil*, e.g., the ampicillin resistance gene of *E. coli* and *S. cerevisiae* trpl gene, which provides a selection marker for a mutant strain of yeast lacking the ability to grow in tryptophan, and a promoter derived from a highly expressed yeast gene to induce transcription of a structural sequence downstream. The presence of the trpl lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp gene and origin of replication) and yeast DNA sequences including a glucose-repressible ADH2 promoter and α-factor leader, which directs secretion of heterologous proteins, can be inserted between the promoter and the structural gene to be expressed (Kurjan et al., *Cell* 30:933, 1982; and Bitter et al., *Proc. Natl. Acad. Sci. USA* 81:5330, 1984). The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 $\mu$g/ml adenine and 20 $\mu$g/ml uracil.

Host strains transformed by vectors comprising the ADH2 promoter may be grown for expression in a rich medium consisting of 1% yeast extract 2% peptone, and 1% glucose supplemented with 80 $\mu$g/ml adenine and 80 $\mu$g/ml uracil. Derepression of the ADH2 promoter occurs upon exhaustion of medium glucose. Crude yeast supernatants are harvested by filtration and held at 4° C. prior to further purification. Various mammalian or insect cell culture systems can be employed to express recombinant protein. Baculovirus systems for production of heterologous proteins in insect cells are reviewed by Luckow and Summers, *Bio/Technology* 6:47 (1988).

Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese Hamster Ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' to 3' nontranslated sequences, such as necessary ribosome binding sites, a poly-adenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin or replication (Fiers et al., Nature 273:113, 1978). Smaller or larger SV40 fragments may also be used, provided the approximately 250 bp sequence extending from the Hind III site toward the BgII site located in the viral origin or replication is included. Exemplary vectors can be constructed as disclosed by Okayama and Berg (*Mol. Cell. Biol.* 3:280, 1983).

Preferred eukaryotic vectors for expression of mammalian DNA include pIXY321 and pIXY344, both of which are yeast expression vectors derived from pBC102.K22(ATCC 67,255) and contain DNA sequences from pBR322 for selection and replication in *E. coli* (Apr gene and origin of replication) and yeast.

Purified mammalian fusion proteins or analogs are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix.

Finally, one or more reverse phase high performance liquid chromatography (RP-HPLC) media, e.g., silica gel having pendant methyl or other aliphatic groups, can be employed to further purify a fusion protein composition. Some or all of the foregoing purification steps, in various combinations, can also be employed to provide a homogenous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can be disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large scale fermentation can be purified by methods analogous to those disclosed by Urdal et al. (*J. Chromatog.* 296:171, 1984).

Fusion protein synthesized in recombinant culture is characterized by the presence of non-human cell components, including proteins, in amount and of a character which depend upon the purification steps taken to recover the fusion protein from the culture. These components ordinarily will be of yeast, prokaryotic or non-human higher eukaryotic origin and preferably are present in innocuous contaminant quantities, on the order of less than about 5 percent by scanning densitometry or chromatography. Further, recombinant cell culture enables the production of the fusion protein free of proteins which may be normally associated with EPO as they are found in nature in their respective species of origin, e.g., in cells, cell exudates or body fluids.

The present invention further relates to pharmaceutical compositions comprising a fusion protein and a physiologically-compatible carrier. Such carriers are described in U.S. Pat. No. 5,580,853, the teachings of which are herein incorporated by reference in their entirety. Pharmaceutical compositions suitable for administration comprise the fusion protein in an effective amount and a physiologically acceptable carrier. An effective amount, as used herein, is defined as that quantity which alleviates, to any degree, or eliminates the condition for which the mammal is being treated.

The carriers will be non-toxic to recipients at the dosages and concentrations employed. The formulation used will vary according to the route of administration selected (e.g., solution, emulsion, capsule). For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. See, generally, *Remington's Pharmaceutical Science,* 16th Edition, Mack, Ed. (1980). For inhalation, the compound can be solubilized and loaded into a suitable dispenser for administration (e.g., an atomizer, nebulizer or pressurized aerosol dispenser). Fusion proteins can be administered individually, together or in combination with other drugs or agents (e.g., other chemotherapeutic agents, immune system enhancers).

Fusion protein compositions can be used to enhance proliferation, differentiation and functional activation of hematopoietic progenitor cells, such as bone marrow cells. Fusion protein compositions can also be used in the treatment of cancers or cellular growth deficiencies. Specifically, compositions containing the fusion protein may be used to increase peripheral blood leukocyte numbers and increase circulating granulocyte counts in myelosuppressed patients. To achieve this result, a therapeutically effective quantity of a fusion protein composition is administered to a mammal, preferably a human, in association with a pharmaceutical carrier or diluent.

The present invention will now be further illustrated by the following exemplification, which is not meant to be limiting in any way.

EXEMPLIFICATION: PRODUCTION OF AN EPO-EPO FUSION PROTEIN

The methods and materials described below were used in carrying out the work described.

CONSTRUCTION OF THE EPO-EPO DINER

Figure 1:
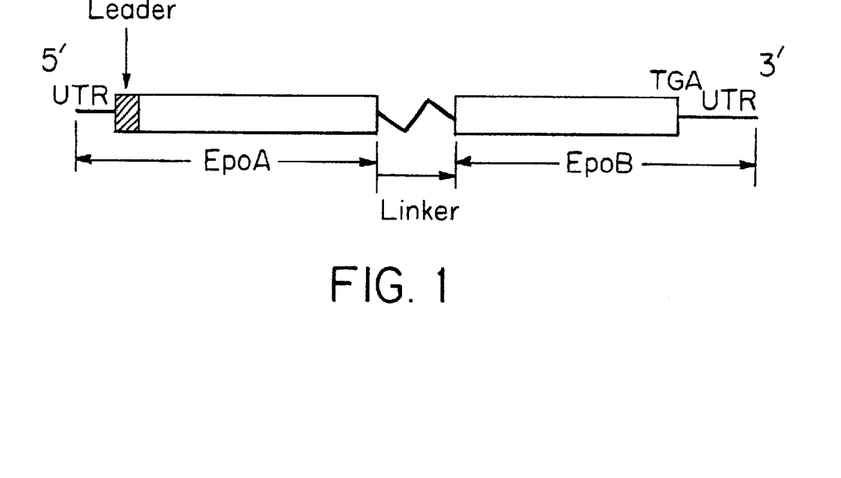
FIG. 1 is a diagram showing an EPO-EPO dimer DNA construct comprising an EPO A cDNA linked to an EPO B cDNA via a linker sequence.
Figure 2:
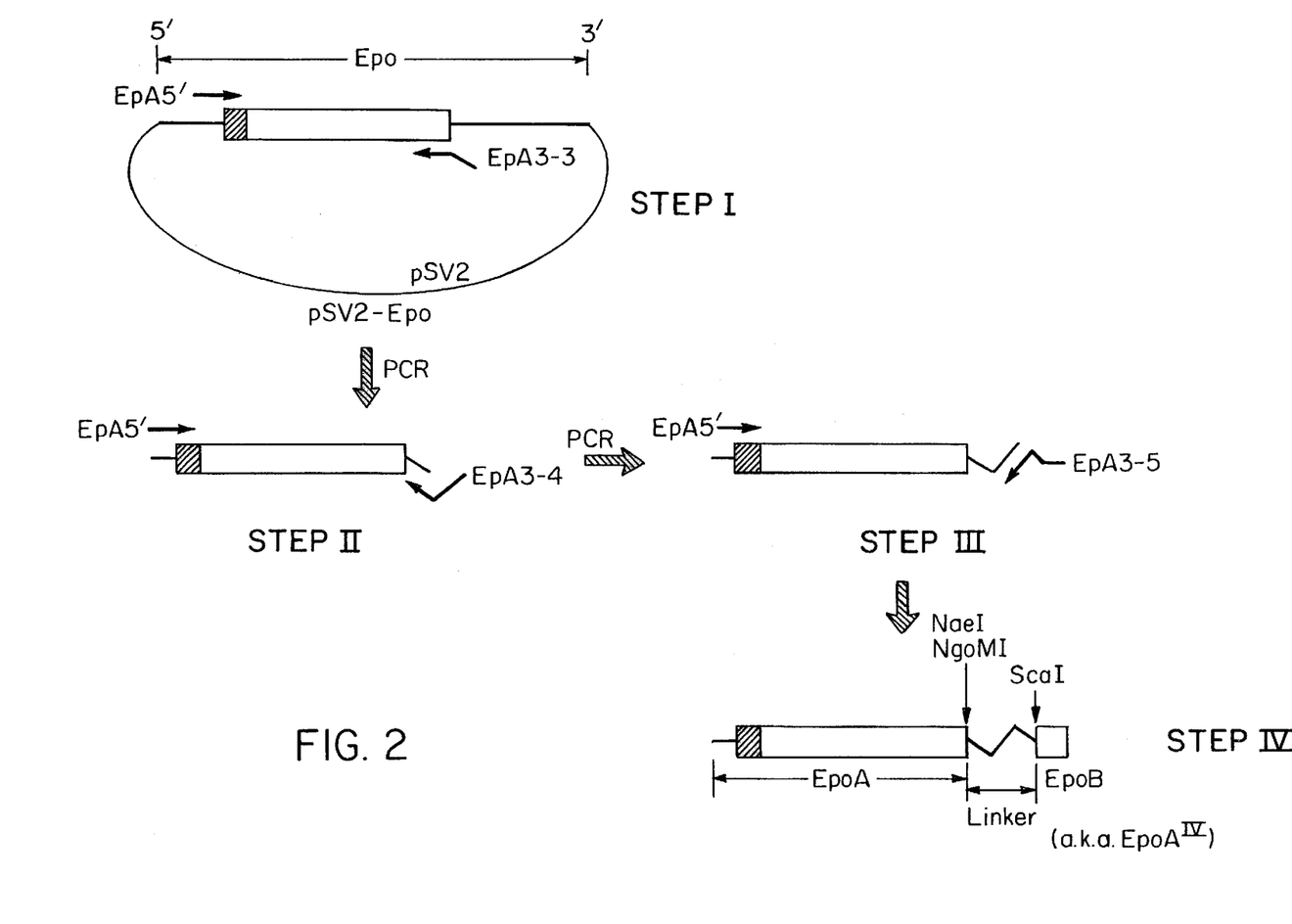
FIG. 2 is a diagram showing production of EPO A DNA and sequential elongation of linking DNA strand encoding [gly-gly-gly-gly-ser]$_3$ (SEQ ID NO.9) using PCR.
Figure 4:
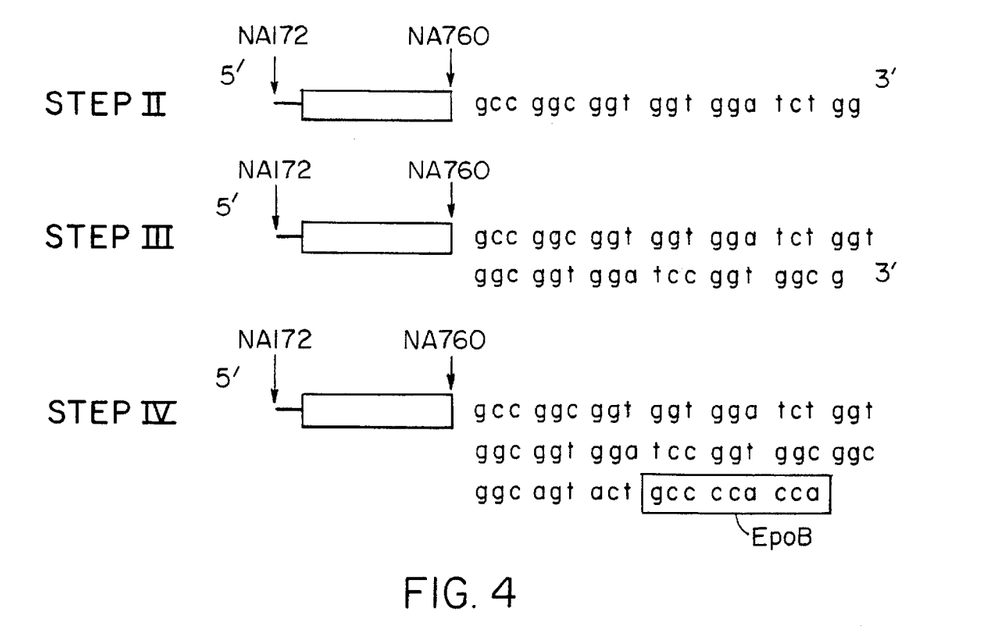
FIG. 4 is a diagram showing the end product of each of steps II–IV of FIG. 2.
Figure 5:
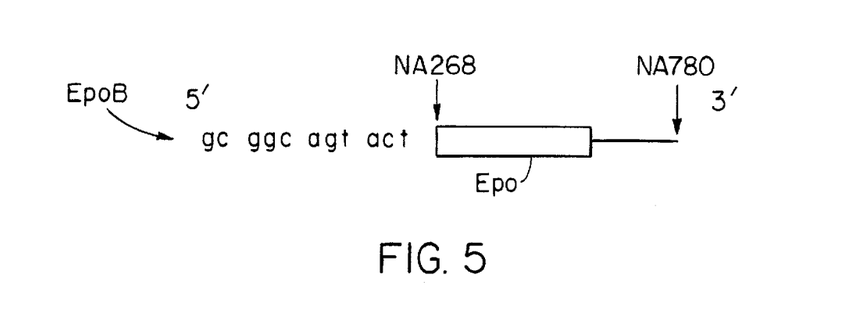
FIG. 5 is a diagram showing the end product of FIG. 3.

An EPO-EPO fusion protein was constructed by linking two strands of EPO cDNA with a DNA strand encoding the following polypeptide: AGGGGSGGGGSGGGGST (SEQ ID NO: 1)(FIG. 1). The nucleotide sequence of wild type erythropoietin can be obtained from Jacobs, K., et al., Nature 323:806(1985), which is herein incorporated by reference in its entirety. The linking DNA strand was sequentially lengthened to the proposed length by using psv2-EPO (FIG. 2) as template and 3' primers with appropriately extended 3' ends (FIG. 2). The initial preceeding EPO DNA strand (FIG. 4) contains 10 nucleotides in the 5' untranslated region, a leader sequence (Jacobs, K., et al., *Nature* 323:806(1985)), an EPO cDNA coding sequence, and no STOP codon. Additional nucleotides attached to the 3' end were: GCCGGCGGTG-GTGGATCTGG (SEQ ID NO: 2). The EPO DNA strand after the linker (EPO B DNA; FIG. 5) contains no leader sequence but has a STOP codon and 17 nucleotides in the 3' untranslated region. Half a NaeI restriction site was designed into the 3' end of EPO A DNA and half a ScaI restriction site into the 5' end of EPO B DNA.

Figure 3:
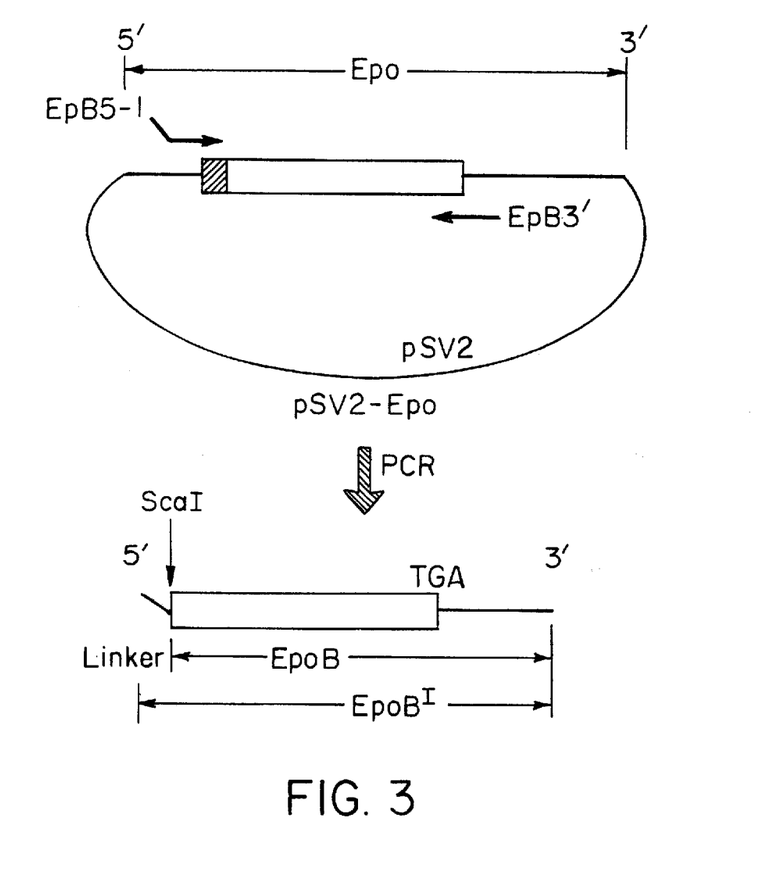
FIG. 3 is a diagram showing production of EPO B DNA using PCR.

EPO A (FIG. 2) and EPO B (FIG. 3) DNA were produced by the using the Polymerase Chain Reaction (PCR) and a human EPO cDNA plasmid, psv2-EPO (Chern Y. J., et al., *Eur J Biochem* 202:225(1991)) as template.

Primers used to produce EPO A are as follows: 5'-AGGCGCGGAGATGGGGGTGCAC (SEQ ID NO: 3) (EpA 5'), 3'-CCAGATCCACCACCGCCGGCTCTGTCCCCT GTCCTGCAGG (SEQ ID NO: 4) (EpA3–3), 3'-CGCCACCGGATCCACCGCCACCAGATCCAC CACCGCCGGC (SEQ ID NO: 5) (EpA3–4), and 3'-TGGTGGGGCAGTACTGCCGCCGCCACCGGA TCCACCGCC (SEQ ID NO: 6) (EpA3–5).

Primers used to produce EPO B are as follows: 5'-GCGGCAGTACTGCCCCACCACGCCTCATCTG TGACAGC (SEQ ID NO: 7) (EpB 5–1) and 3'-CAGGTGGACACACCTGGTCATC (SEQ ID NO: 8) (EpB 3').

PCR reactions (50 μl) contained the following components: 0.5 μM of 5' primer or 3' primer; 10 ng psv2-EPO; 200 μM of DATP, dCTP, dGTP, or dTTP; 20 mM Tris-HCl (pH 8.0); 2 mM $MgCl_2$; 10 mM KCl; 6 mM $(NH_4):SO_4$; 0.1% Triton X-100; 10 μg/ml nuclease-free BSA; and 2.5 U Pfu DNA Polymerase (Stratagene). The reactions were overlaid with mineral oil (50 μl; Molecular Biology Grade, Sigma) and subjected to 25 cycles of 94° C. for 1 min (denaturation), of 52° C. for 1 min (annealing) and of 72° C. for 1 min (extension) in a Perkin Elmer DNA Thermal Cycler 480.

Next, the DNA sequences of the PCR products were determined. First, the PCR products were purified from a 1% agarose gel using the QIAQUICK™ Gel Extraction Kit. They were then ligated to pCR-blunt, in which the reactions contained an insert to vector molar ratio of 10 to 1. The ligation reactions (10 μl) contained the gel-purified PCR products, 25 ng of PCR-blunt, 1X ligation buffer and 4 U of T4 DNA ligase (ZERO BLUNT™ PCR Cloning Kit, Invitrogen). Incubations were carried out for 1 hour at 16° C.

Cells used for expression were TOP OTM Competent Cells (Invitrogen) and were transformed according to procedure established by Invitrogen: 2 μl of β-mercaptoethanol was added to the cells on ice, mixed by gentle swirling with a pipette tip, followed by 2 μl of the ligation described in the preceding paragraph. This mixture was then incubated on ice for 30 min, followed by exactly 45 seconds at 42° C. The vial was then placed on ice for 2 min. 250 μl of pre-warmed (37° C.) SOC medium containing 2% tryptone, 0.5% yeast extract, 10 mM NaCl, 2.5 mM KCl, 10 mM $MgCl_2$, 10 mM $MgSO_4$, and 20 mM glucose was added and the cells shaken for 1 hr at 37° C. 50 μl of a 1:5 dilution of transformed cells were plated on LB (Miller's modification, Sigma) agar plates containing 50 Mg/ml kanamycin. The plates were incubated at 37° C. overnight. Colonies were plucked and 2.5 ml LB containing 50 μg/ml kanamycin were inoculated with these colonies. Plasmid DNA were prepared from the overnight cultures using Promega's WIZARD PLUS MINI-PREPS™ DNA Purification System. Clones were analyzed by restriction digest fragment analysis.

Figure 6:
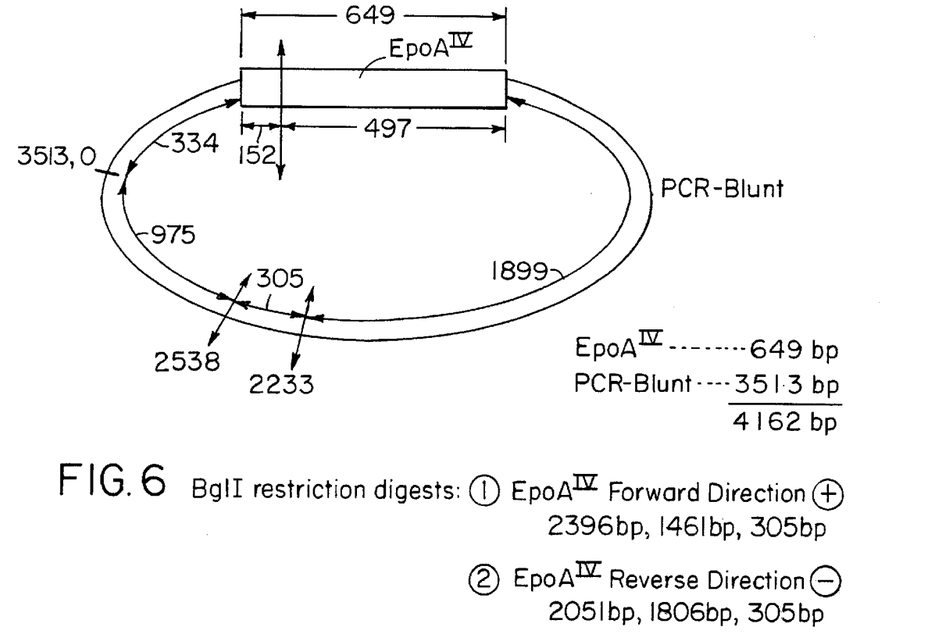
FIG. 6 is a diagram showing the restriction digest of pCRBlunt-EPO A$^{IV}$ with Bgl I.
Figure 7:
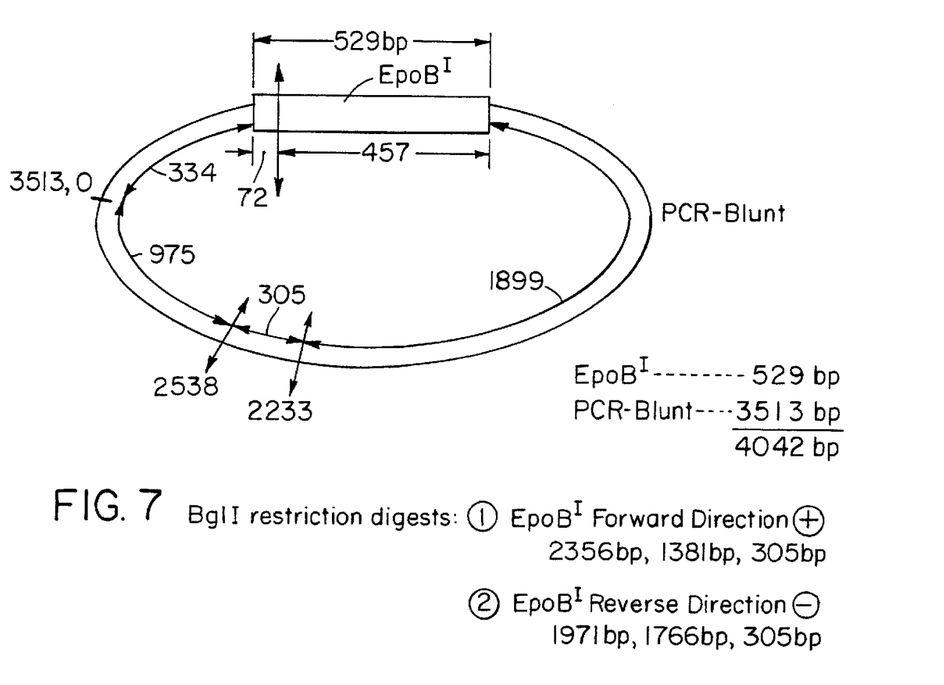
FIG. 7 is a diagram showing the restriction digest of pCRBlunt-EPO B$^I$ with Bgl I.

The pCRBlunt-EPO A and pCRBlunt-EPO B DNA clones were digested with BglI, which gave unique-sized fragments for a correctly inserted DNA and an insert oriented in the reverse direction (FIGS. 6 and 7). Clones with inserts in the reverse direction were chosen and larger amounts (from 100 ml of LB/50 μg/ml kanamycin) of DNA plasmids prepared using Promega's WIZARD PLUS MAXIPREPS™ DNA purification system. Clones with inserts in the "forward" direction would also have produced the proposed EPO-EPO DNA.

Figure 8:
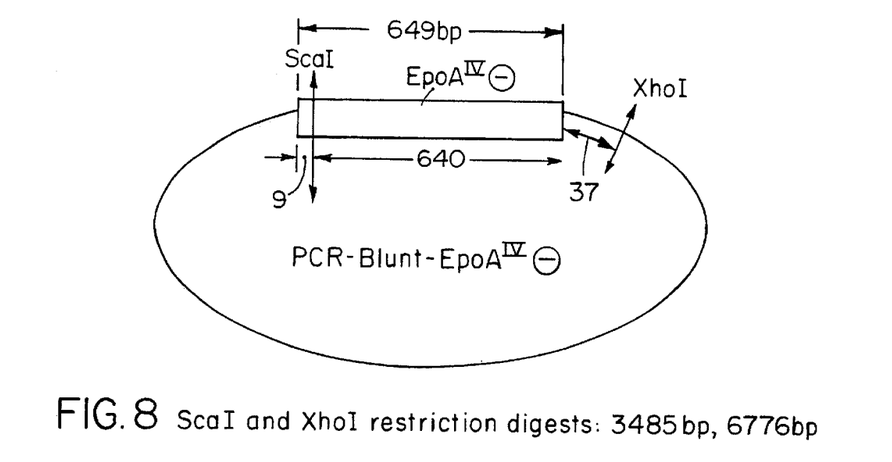
FIG. 8 is a diagram showing the restriction digest of pCRBlunt-EPO A$^{IV}$(−).
Figure 9:
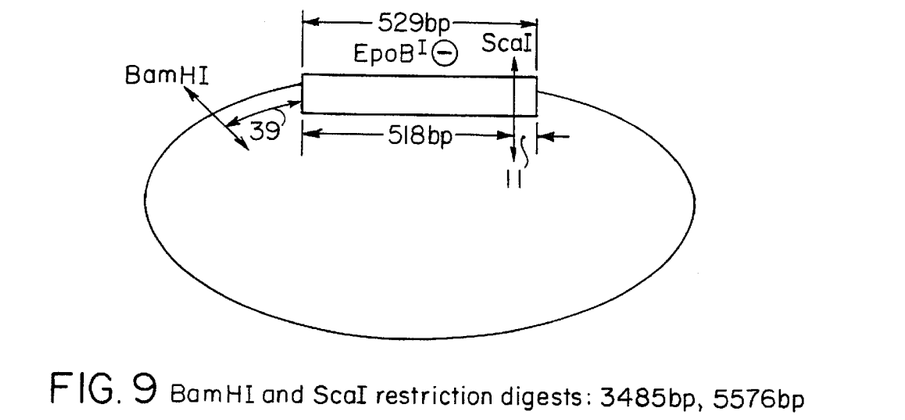
FIG. 9 is a diagram showing the restriction digest of pCRBlunt-EPO B$^I$(−).
Figure 10:
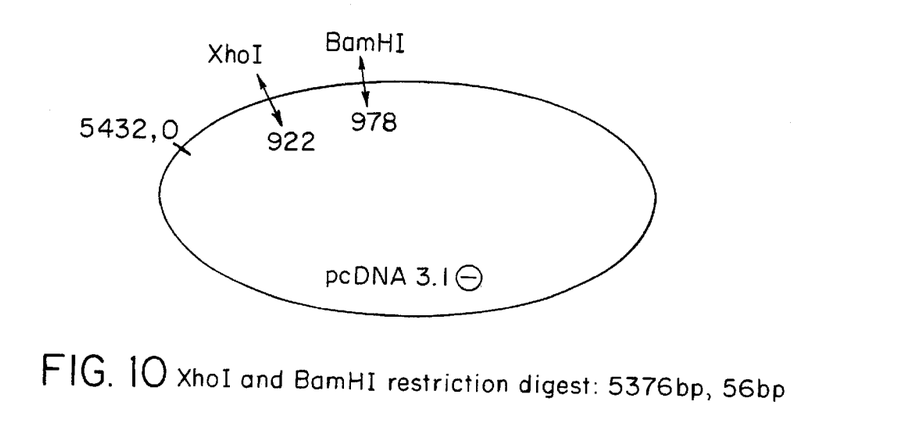
FIG. 10 is a diagram showing the Xho I and BamH I restriction digest of pcDNA3.1(−).
Figure 11:
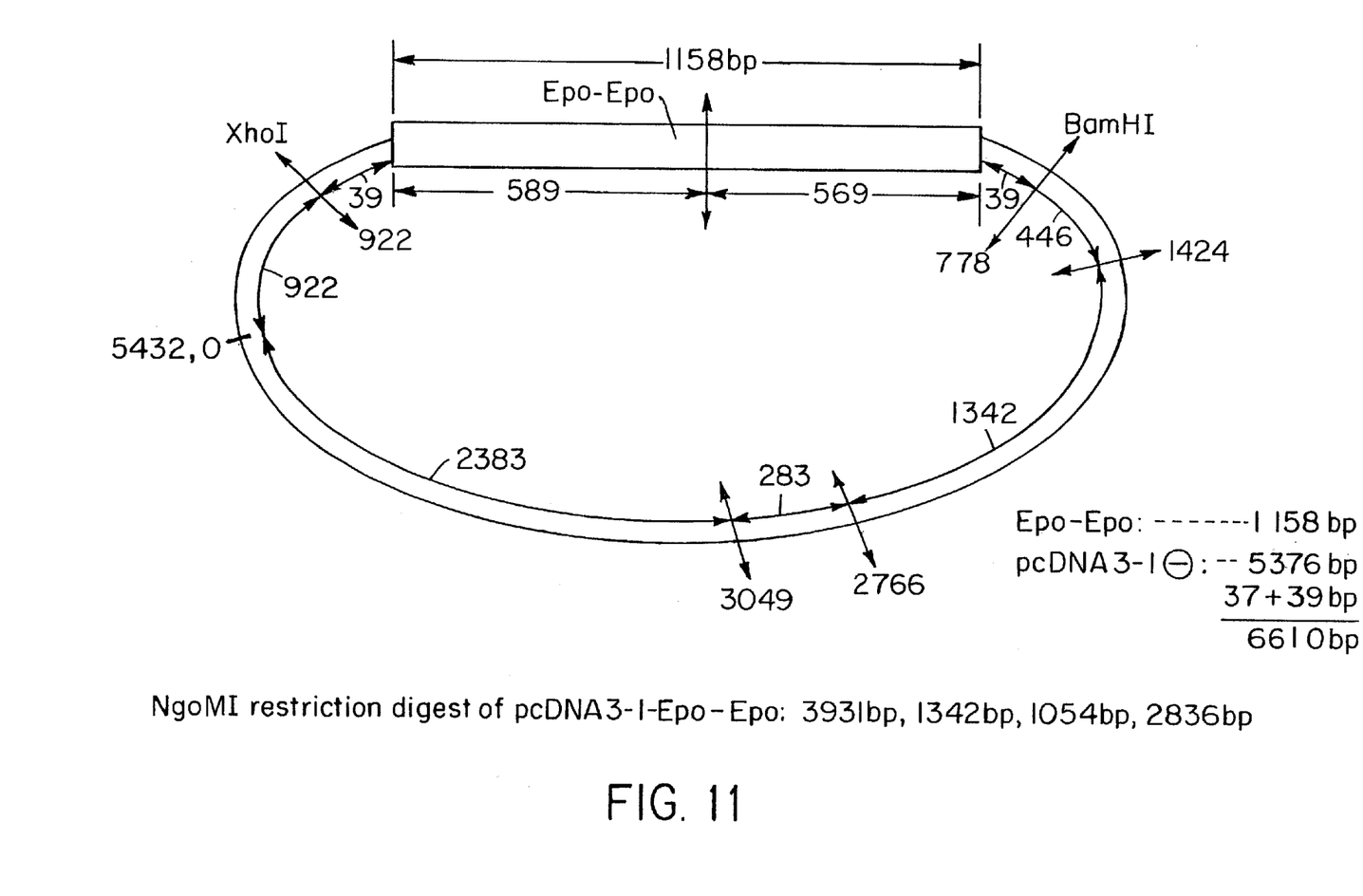
FIG. 11 is a diagram showing the restriction digest of pcDNA3.1-EPO-EPO.

EPO A DNA was linked to EPO B DNA using the procedure described as follows. pCRBlunt-EPO A(–) was digested with Sca I and Xho I and the 677 bp fragment gel purified (FIG. 8). pCRBlunt-EPO B(–) was digested with BamHI and ScaI and the 557 bp fragment gel purified (FIG. 9). The EPO A 677 bp fragment was then ligated to the EPO B 557 bp fragment in a 1:1 molar ratio of EPO A 677 bp fragment to EPO B 557 bp fragment. Ligations were carried out overnight at 16° C. The ligated EPO A/EPO B DNA fragments were purified using QIAQUICK™ Gel Extraction Kit then ligated to pcDNA2.1(–) which had previously been digested with XhoI and BamHI and gel purified (FIG. 10). The ligation reaction contained a 5:1 molar ratio of DNA insert to pcDNA3.1(–). The incubation was carried out overnight at 16° C. Clones were picked from ampicillin-resistant colonies by restriction digest analysis (FIG. 11), produced in microgram quantities, and used to transfect COS I cells.

TRANSIENT EXPRESSION OF EPO DIMER IN COS I CELLS

COS I cells were grown to 70% confluency in Dulbecco's Modified Eagle Medium, high glucose (4.5 g/L; Gibco), 10% fetal bovine serum (Hyclone) in the presence of 100 U penicillin, 100 μg streptomycin, 250 ng Fungizone per ml of tissue culture medium (antibiotic-antimycotic cocktail from Gibco) at 37° C. and 10% $CO_2$. The cells were harvested by trypsinizing using 0,05% Trypsin, 0.53 mM EDTA (Gibco) and washing twice with phosphate buffered saline (PBS)/6 mM glucose solution. Cells were suspended in the above PBS/glucose buffer to a concentration of $2 \times 10^6$ cells/ml. 0.5 ml of cells were placed in electroporation cuvettes (0.4 cm gap, Bio-Rad) and 10 Mg of pcDNA/EPO-EPO added. The cells were electroporated under the following conditions: voltage=0.3 kV, field strength=0.75 kV/cm, capacitor=250 μF, and resistor=none (Pulse controller set at Ω). Cells were plated in 30 ml of pre-warmed DMEM, high glucose, 10% FBS and incubated for 72 h at 37° C. and 10% $CO_2$. The controls used were 10 μg of pcDNA-EPO and 10 μg of pcDNA 3.1(–).

The conditioned media were collected, centrifuged at 13,800×g for 10 min at 4° C. 1 ml aliquots of each conditioned media were dialyzed against Mimimum Essential Medium α overnight with 3×changes of medium. These samples were assayed for EPO activity by the method of Krystal as described in U.S. Pat. No. 5,580,853, which is herein incorporated by reference in its entirety. The conditioned medium of cells transfected with pcDNA/EPO-EPO was 45–72 U/ml in an in vitro bioassay, and the medium from cells transfected with pcDNA-EPO was 5 U/ml. Conditioned media from cells transfected with pcDNA and untransfected cells showed no EPO activity.

IN VIVO ACTIVITY OF pcDNA/EPO-EPO

Conditioned medium from cells transfected with pcDNA/EPO-EPO was used to inject mice (B6C3F1 strain, female, 18 g, Jackson Labs). The haematocrits of these mice were measured prior to administering EPO-EPO. 300 U of EPO-EPO per kg of mouse were injected subcutaneously on day 1, day 3, and day 5. Their haematocrits were measured on day 7. Mouse #1 showed an increase haematocrit of 4.5% and mouse #2 an increase of 1.5%.

A more extensive study was subsequently conducted with four mice in a control group and four mice in an experimental group (B6C3F1 strain, female, 18 g, Jackson Labs). The control group was treated with 200 μl of medium on day 1, day 3, and day 5, while the experimental group was treated with 300 U/kg of fusion protein pcDNA/EPO-EPO in 200 μl of medium on day 1 only. The haematocrits of all mice in the study were measured prior to administration (day 0) and following administration (day 8).

The results are summarized in Table 1 and Table 2 below. The mean increase for the experimental group from 46.2 on day 0 to 48.8 on day 8 represents the equivalent of one unit of blood.

TABLE 1

HEMATOCRITS OF CONTROL GROUP

| Mouse No. | Day 0 | Day 8 |
| --- | --- | --- |
| 1 | 47.5 | 48.0 |
| 2 | 50.0 | 48.0 |
| 3 | 46.5 | 47.5 |
| 4 | 46.0 | 45.0 |
| Mean | 47.5 | 47.0 |

TABLE 2

HEMATOCRITS OF EXPERIMENTAL GROUP

| Mouse No. | Day 0 | Day 8 |
| --- | --- | --- |
| 1 | 48.5 | 50.5 |
| 2 | 47.0 | 50.0 |
| 3 | 45.0 | 47.0 |
| 4 | 44.0 | 48.0 |
| Mean | 46.0 | 49.0 |

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant fusion protein comprising two or more erythropoietin molecules.

2. The recombinant fusion protein of claim 1, wherein said erythropoietin molecules are linked by a peptide linker.

3. The recombinant fusion protein of claim 2, wherein said peptide linker allows the erythropoietin molecules to rotate freely relative to each other.

4. The recombinant fusion protein of claim 2, wherein said peptide linker is from about 10 amino acids to about 20 amino acids in length.

5. The recombinant fusion protein of claim 3, wherein said peptide linker is about 15 amino acids in length.

6. The recombinant fusion protein of claim 4, wherein said amino acids are selected from the group consisting of glycine, serine, asparagine, threonine and alanine.

7. A nucleic acid comprising a nucleotide sequence which encodes a recombinant fusion protein comprising two or more erythropoietin molecules.

8. A vector comprising said nucleic acid of claim 7.

9. A host cell transfected with the vector of claim 8.

10. A pharmaceutical composition comprising said recombinant fusion protein of claim 1 and a pharmaceutically acceptable carrier.

11. A method for producing a recombinant fusion protein comprising culturing the host cell of claim 9, in a suitable medium to produce the recombinant fusion protein.

12. A method of treating or preventing anemia in a mammal comprising administering to the mammal said recombinant fusion protein of claim 1, wherein anemia is treated or prevented.

13. The recombinant fusion protein of claim 1 that has a prolonged plasma half-life.

* * * * *